United States Patent
Wojke et al.

(10) Patent No.: US 10,525,188 B2
(45) Date of Patent: Jan. 7, 2020

(54) METHOD OF PURGING GAS BUBBLES IN AN EXTRACORPOREAL BLOOD CIRCUIT

(71) Applicant: FRESENIUS MEDICAL CARE DEUTSCHLAND GMBH, Bad Homburg (DE)

(72) Inventors: Ralf Wojke, Bad Homburg (DE); Paul Wieneke, Muenster (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 77 days.

(21) Appl. No.: 15/501,541

(22) PCT Filed: Aug. 5, 2015

(86) PCT No.: PCT/EP2015/001618
§ 371 (c)(1),
(2) Date: Feb. 3, 2017

(87) PCT Pub. No.: WO2016/020061
PCT Pub. Date: Feb. 11, 2016

(65) Prior Publication Data
US 2017/0224899 A1 Aug. 10, 2017

(30) Foreign Application Priority Data
Aug. 5, 2014 (DE) .................. 10 2014 011 675

(51) Int. Cl.
*A61M 1/36* (2006.01)
(52) U.S. Cl.
CPC ........ *A61M 1/3629* (2014.02); *A61M 1/3626* (2013.01); *A61M 1/3643* (2013.01);
(Continued)
(58) Field of Classification Search
None
See application file for complete search history.

(56) References Cited

U.S. PATENT DOCUMENTS

| 4,485,629 A | 12/1984 | Le Goff |
| 5,591,344 A * | 1/1997 | Kenley .................. A61L 2/04 210/636 |

(Continued)

FOREIGN PATENT DOCUMENTS

| DE | 102007007198 | 8/2008 |
| DE | 102011110472 | 1/2013 |

(Continued)

OTHER PUBLICATIONS

EP1892000 Machine Translation—Moll et al—Feb. 27, 2008 (Year: 2008).*

*Primary Examiner* — Bradley R Spies
(74) *Attorney, Agent, or Firm* — Jacobson Holman, PLLC.

(57) ABSTRACT

The invention relates to a method of purging gas bubbles from at least one target zone of an extracorporeal blood circuit, preferably of an extracorporeal blood circuit of a dialysis machine, with a flushing liquid, wherein the flow rate and/or the pressure of the flushing liquid in the extracorporeal blood circuit is/are inconstant at least at times during the flushing process; and/or wherein the flow rate of the flushing liquid in the extracorporeal blood circuit lies above a range of possible flow rates at least at times during the flushing process, which range is used during the treatment for the blood. The invention furthermore relates to an extracorporeal blood treatment unit having an extracorporeal blood circuit, a pump and a control unit, with the control unit being configured to carry out a flushing process in accordance with the invention. The invention furthermore relates to an extracorporeal blood treatment unit having an extracorporeal blood circuit, a pump and a control unit, with the control unit being configured such that the conveying (Continued)

speed for blood is slowly increased after a standstill of the pump or after an operation of the pump at throttled speed.

11 Claims, 1 Drawing Sheet

(52) U.S. Cl.
CPC ... *A61M 1/3644* (2014.02); *A61M 2205/3334* (2013.01); *A61M 2205/3337* (2013.01); *A61M 2205/3365* (2013.01)

(56) References Cited

U.S. PATENT DOCUMENTS

| | | | |
|---|---|---|---|
| 2004/0184953 A1 | 9/2004 | Litzie et al. | |
| 2012/0265117 A1* | 10/2012 | Fava | A61M 1/3647 604/6.09 |
| 2013/0319917 A1 | 12/2013 | Fava et al. | |

FOREIGN PATENT DOCUMENTS

| | | |
|---|---|---|
| EP | 0543172 | 5/1993 |
| EP | 1892000 | 2/2008 |
| EP | 2462965 | 6/2012 |

\* cited by examiner

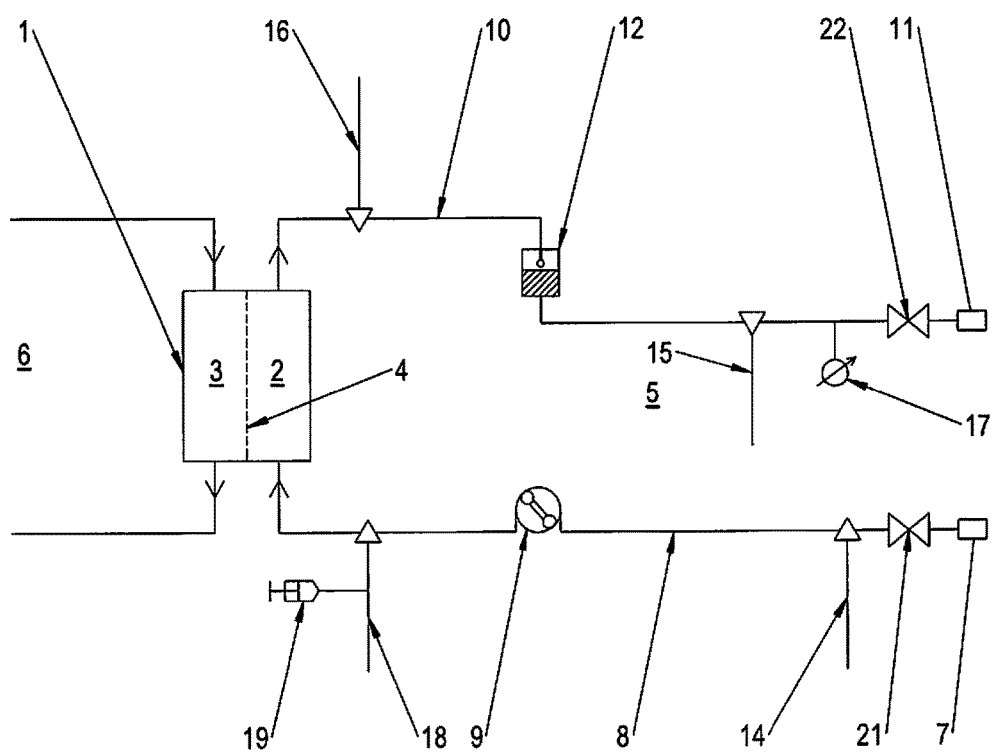

METHOD OF PURGING GAS BUBBLES IN AN EXTRACORPOREAL BLOOD CIRCUIT

The invention relates to a method of purging gas bubbles from a target zone of an extracorporeal blood circuit as well as to an extracorporeal blood treatment unit.

Microbubbles are gas bubbles having a diameter of a few μm which as a rule are no longer visible due to their small size. They arise at different points and under different conditions in extracorporeal blood circuits, inter alia by the discharge of blood-soluble gases or by air entry at very small leaks in the vacuum region of the extracorporeal circuit, and adhere to the inner surface of the extracorporeal hose system or of the blood treatment unit. Their effects when they are detached and infuse into the human body are greater than previously presumed. For example, microbubbles were found in vital organs such as the lung, heart and brain of dialysis patients.

Observations at dialyzers with the aid of a microbubble detector allow a number of possible sources for microbubbles to be recognized. It was inter alia observed that an increased entry of microbubbles into the patient takes place in the first minutes of the treatment. At the start, the mean microbubble flow can be an order of magnitude higher than during the remaining treatment. In addition, there are potentially air collections in the extracorporeal circuit which can serve as sources and reservoirs for later microbubble formation. Air collections can, for example, be present in the dialyzer, in the hose segment of the blood pump, in the venous drip chamber, in heparin syringes and in other injection syringes, in supplying lines (e.g. in a heparin hose) and in further interfaces (e.g. Luer connections). The vacuum in the intake region of the pump generally promotes air inputs. Furthermore, an increased number of microbubbles was observed during a pressure holding test in which the dialysis fluid is temporarily no longer refreshed and the blood in the dialyzer capillaries is no longer washed around with fresh, degased dialysis fluid.

Microbubbles can only be separated with limitations in the venous chamber due to their small size and their small buoyancy and can only be conditionally recognized by the prescribed protection system for avoiding air infusion.

It is the underlying object of the invention to reduce the number of microbubbles in extracorporeal blood circuits or to reduce the infusion of microbubbles into the patient's body.

Against this background, the invention proposes a method of purging gas bubbles from at least one target zone of an extracorporeal blood circuit using a flushing fluid, wherein the flow rate and/or the pressure of the flushing liquid in the extracorporeal blood circuit is inconstant at least at times during the flushing process, and/or wherein the flow rate of the flushing liquid in the extracorporeal blood circuit lies outside a range of possible flow rates at least at times during the flushing process, which range is used during the treatment for the blood. The latter feature can mean that the flow rate of the flushing liquid in the extracorporeal blood circuit lies above a range of possible flow rates at least at times during the flushing process, which range is used during the treatment for the blood. There is further the possibility of flow reversal, for example.

In accordance with the prior art, the flushing of the extracorporeal blood circuit only runs at a small and constant flow rate or at a constant liquid pressure. In this respect, large bubbles are admittedly separated, e.g. in the venous chamber, but the quantity of microbubbles is hardly reduced. It is therefore proposed in accordance with the invention to adapt the blood pump rate during the flushing such that the microbubbles can be removed more easily.

In an embodiment, the extracorporeal blood circuit is that of a dialysis machine. The extracorporeal blood circuit of a dialysis machine comprises an arterial line, a blood pump, a dialyzer and a venous line. An arterial port for connection to a patient is arranged in the arterial line. A venous port for connection to the patient is arranged in the venous line. Furthermore, a use of the method is also conceivable in other extracorporeal treatment systems, for example in ultrafiltration devices and heart-lung machines.

In an embodiment, the flushing liquid is conveyed through the target zone by means of a pump and the variation of the flow rate and/or of the pressure takes place by a change in the conveying rate of the pump.

In an embodiment, the change of the conveying rate takes place by a switching on and switching off of the pump or a throttling and an increasing of the pump speed. A throttling is to be understood as a powering down of the pump to a conveying rate of greater than 0, whereas a switching off is understood as a complete stop. Correspondingly, the increase starts from a conveying rate of greater than 0, whereas the switching on starts from a conveying rate equal to 0.

In an embodiment, the pump is a blood pump arranged in the extracorporeal blood circuit or a flushing pump arranged outside the extracorporeal blood circuit. A flushing pump can, for example, be arranged in a feed line of flushing liquid.

In an embodiment, the extracorporeal blood circuit has at least one clamp or a valve and the variation of the flow rate and/or of the pressure takes place by a control of the clamp. The term of a clamp in the present case also comprises a valve which can throttle or stop the throughflow of flushing liquid into, through or out of the extracorporeal blood circuit. The extracorporeal blood circuit can, for example, have an arterial clamp and/or a venous clamp. An inflow or outflow of flushing liquid differing from the arterial port or from the venous port can also have a clamp. A variation of the pressure and/or of the flow rate can be achieved, for example, by closing a clamp at the outflow of the flushing liquid (venous port or separate outflow) and by a backing up of liquid and a subsequent opening. A variation can furthermore also be achieved by closing a clamp at the inflow of the flushing liquid and a subsequent opening and abrupt letting in of the flushing liquid.

In an embodiment, the flow rate and/or the pressure of the flushing liquid is increased and reduced in bursts. A periodic increase and decrease of the flow rate and/or of the pressure is possible over a specific time period, for example. The bursts can have a duration of, for example, 0.1 s to 5 s.

In an embodiment, the bursts show a continuous or abrupt build-up and a continuous or abrupt drop in the flow rate and/or in the pressure of the flushing liquid. For example, a continuous pressure build-up and a substantially abrupt pressure drop can be achieved in that a clamp at the outflow side or a venous clamp is closed for the pressure build-up and is opened again for the subsequent pressure drop. On an optionally periodic change in the conveying power of the pump, a determination can be made by means of the pump control as to how abruptly the build-up or drop of the flow rate and/or of the pressure is.

In an embodiment, the amplitude of the bursts is selected such that the flow rate and/or the pressure of the flushing liquid varies between valleys and peaks by at least a factor of 1.3, a factor of 1.5 or a factor of 2. A good efficiency in the detachment of gas bubbles is ensured by a certain minimum magnitude of the amplitude of the bursts.

In an embodiment, the flow rate of the flushing speed in the extracorporeal blood circuit during the flushing process is larger than 550 ml/min or larger than 700 ml/min at least at times. In many cases, a flow of between 200 ml/min and 550 ml/min is selected during an extracorporeal blood treatment, in particular when hose systems having an internal diameter of between 3 and 5 mm are used. A higher flow rate during the flushing process can result in a better detachment of gas bubbles.

In an embodiment, the method can be carried out within the framework of the priming procedure for the extracorporeal blood circuit and can, for example, represent the final step of the priming procedure.

In an embodiment, the method is carried out during a treatment interruption, in particular during a pressure holding test. The method can be triggered manually or automatically. Examples for trigger conditions comprise a periodic triggering (e.g. with interval values of 30 minutes to 2 hours) or a triggering in response to specific sensor reports (e.g. a measured value of the bubble detector exceeds a limit value, with it then being assumed that the detected number of bubbles and the non-detected number of bubbles increase in parallel) or events (e.g. start of a pressure holding test). The flushing can take place over a predefined time period (e.g. with a duration of between 1 and 15 minutes) or can be determined manually or automatically on the basis of different parameters. The coupling to a duration of another process such as a pressure holding test is also conceivable.

The invention furthermore relates to an extracorporeal blood treatment unit having an extracorporeal blood circuit, a pump and a control unit, with the control unit being configured to carry out a flushing process in accordance with the invention.

In an embodiment, the control unit is configured so that it automatically triggers the process within the framework of the priming of the extracorporeal blood circuit. The process can, for example, represent the final priming step.

In an embodiment, the control unit is configured so that it interrupts the treatment before the carrying out of the flushing process in accordance with the invention and/or so that it triggers the process during an interruption of the treatment and/or so that it automatically continues the treatment after the carrying out of the process. The control unit can, for example, be configured to interrupt the treatment just to carry out the process. The interruption takes place periodically, for example (e.g. with interval values from 30 minutes to 2 hours) or in response to specific sensor reports, for example reports of a gas bubble sensor arranged in the venous line. The control unit can furthermore be configured so that the process is triggered when the treatment is anyway interrupted. The process can be triggered, for example, during a pressure holding test. The duration of the process can, for example, correspond to the duration of a simultaneously carried out pressure holding test (e.g. between 1 and 5 minutes).

In an embodiment, the control unit is configured so that it takes account of the quantity of flushing liquid supplied by the process and/or of blood led off by the process in the determination of treatment-specific parameters, in particular in the determination of the ultrafiltration volume.

In an embodiment, the extracorporeal blood circuit has a separate inflow and a separate outflow for flushing liquid which differ from the arterial port and the venous port respectively. A higher flexibility with respect to the onset time of the flushing process in accordance with the invention can thereby be achieved since a purging of gas bubbles can also take place while a patient is connected to the circuit (e.g. during a treatment break or during a pressure holding test). The inflow is preferably arranged in the arterial line, typically upstream or downstream of the blood pump. The outflow is preferably arranged in the venous line. In this embodiment, a flow reversal of the flushing solution would also be conceivable within the framework of the method in accordance with the invention, with the flushing solution preferably being moved in a pulsed manner against the direction of the blood flow.

The invention furthermore relates to an extracorporeal blood treatment unit having an extracorporeal blood circuit, a pump and a control unit, with the control unit being configured such that the conveying speed for blood is slowly increased after a standstill of the pump or after an operation of the pump at throttled speed. The control unit of this blood treatment unit can naturally furthermore be configured to carry out a method in accordance with the invention.

This configuration of the control unit takes place against the background that it was observed that the fast ramping up of the blood pump can have the consequence of an intense increase in the number of microbubbles in the blood leaving the circuit. It is therefore advantageous that the blood pump is ramped up slowly at the start of the treatment or after a stop/reduction during the treatment.

In an embodiment, the control unit is configured so that the conveying speed for blood is slowly increased at the start of the treatment. The pump is stationary as a rule before the start of the treatment.

In an embodiment, the control unit is configured so that the conveying speed for blood is slowly increased after a treatment interruption. The pump can either be stationary or can be operated with a reduced conveying power during a treatment interruption.

In an embodiment, the conveying speed is increased on an optionally linear ramp with an increase of no more than 300 ml/min$^2$ or 200 ml/min$^2$ or 150 ml/min$^2$. This would mean that after a pump stop a desired value for the treatment, for example 400 ml/min, is only reached after at least one minute, for example only after 2 minutes. In this respect, a step-wise increase in the speed or a linear increase is conceivable, e.g. 200 ml/min$^2$ as the blood acceleration in the start-up.

In an embodiment, the extracorporeal blood treatment unit in accordance with the invention is a dialysis machine. The dialysis machine can be suitable and intended for carrying out a hemodialysis, a hemodiafiltration, a hemofiltration and/or just an ultrafiltration. Furthermore, the extracorporeal blood treatment unit in accordance with the invention can be another treatment system, for example an ultrafiltration device or a heart-lung machine. The blood pump and/or the flushing pump can be a peristaltic pump. The flushing liquid can, for example, be a substitution solution or a priming solution. Examples comprise physiological saline and Ringer's solution. The solution can furthermore optionally contain anticoagulation means such as heparin.

Further details and advantages result from the FIGURE described in the following and from the embodiments. The only FIGURE shows a schematic representation of fluid circuits of a dialysis machine in accordance with the invention.

The dialysis machine has a dialyzer 1 which has a blood chamber 2 and a dialysis fluid chamber 3 which are separated from one another by a membrane 4. The blood chamber 2 is a component of an extracorporeal blood circuit 5. The dialysis fluid chamber 3 is a component of a dialysis fluid circuit 6. The blood circuit 5 has an arterial port 7 which is connected to the blood chamber 2 via an arterial line 8. A blood pump 9 is seated in the arterial line 8. The venous end of the blood chamber 2 is connected to the venous port 11 by means of the venous line 10. A drip chamber 12 is located in the venous line.

The extracorporeal blood circuit 5 furthermore has a separate inflow 14 and a separate outflow 15 for flushing liquid. It is alternatively naturally possible and covered by the invention that the flushing liquid enters into the extracorporeal blood circuit via the arterial port 7 and/or leaves it again via the venous port 11. A short-circuit of the arterial and venous ports is conceivable for the purpose of a closed-loop operation. It can nevertheless be advantageous for the flushing liquid charged with microbubbles to flow out of the circuit via the venous port or via a separate outflow. A reversal of the flow of the blood flow direction against the direction of blood flow is conceivable.

The outflow 15 is arranged in the venous line 10 downstream of all existing interfaces of the extracorporeal blood circuit. A postdilution port 16 is shown as an interface by way of example in the FIGURE. An air bubble detector 17 is located between the outflow and the venous port. The inflow is arranged upstream of the blood pump in the arterial line and represents a separate access. As a further interface, the blood circuit comprises a predilution port 18 with an integrated heparin feed line 19. The extracorporeal blood circuit furthermore comprises an arterial clamp 20 and a venous clamp 21. The arterial clamp is arranged between the arterial port 7 and the inflow 14. The venous clamp is arranged between the outflow 15 and the venous port 11. Both the inflow 14 and the outflow 15 are connected to the extracorporeal blood circuit 15 by means of a three-way valve.

The shown extracorporeal blood circuit can be flushed using a process in accordance with the invention. Flushing liquid is thus supplied at the separate inflow 14 and is conveyed through the circuit by means of the blood pump 9. The blood pump is not operated at a constant conveying rate over a certain time period, for example 3 minutes, during the flushing procedure, but the pump speed is rather increased by a factor of 2 and lowered again in brief periodic intervals of around 2 seconds. This results in a periodic change in the flow rate and in the pressure of the flushing liquid in the extracorporeal blood circuit, which in turn promotes the detachment of microbubbles.

The flushing can, for example, be carried out during the priming or during a treatment break. It is, for example, conceivable to carry out the process during the duration of a pressure holding test.

If the process is carried out during the priming, a detachment of already present microbubbles can be brought about by adapting the pump rate in the initial flushing of the extracorporeal circuit. The extracorporeal circuit can be filled to a maximum with degased flushing solution. Pressure bursts can be generated by a repeated stopping and restarting of the blood pump. Microbubbles can be detached from the hose wall and transported away by the flushing solution by this and by a pump rate increased in the further procedure. The flushing solution can be discarded.

If the extracorporeal blood treatment is continued after the standstill of the blood pump after ending the method in accordance with the invention, provision is made within the framework of the described embodiment that the conveying speed of the blood pump is slowly increased at the start of the treatment. A detachment of microbubbles from the extracorporeal line system at the start of treatment can thus be reduced. Provision is specifically made that the conveying speed is increased on a linear ramp with an increase of 200 ml/min$^2$ so that the desired value of 400 ml/min$^2$ is only reached after 2 minutes. Other algorithms for the increase and other desired values are naturally also covered by the invention.

Finally, it can be stated that the partly stationary microbubbles are detached within the framework of the method in accordance with the invention, for example by means of a repeated stop and go of the blood pump and/or by means of a high pump speed and are removed from the extracorporeal circuit by means of present sinks and by means of sinks optionally to be provided in the venous branch of the extracorporeal circuit (e.g. using the UF pump via the dialyzer membrane or via the substitution port or via a further drain in the venous branch). The circuit can be filled to a maximum during the intimal filling of the extracorporeal blood circuit with degased substitution liquid and the air collections and microbubble reservoirs can be attacked and reduced by means of flow and pressure bursts (e.g. by a brief maximum blood pump rate, blocking and releasing the venous clamp, etc.). After a stop of the blood pump before or during the treatment, the blood pump can always be slowly ramped up, e.g. in a ramp with no more than 200 ml/min$^2$, which means that a possible desired rate of 400 ml/min ml/min$^2$ would only be reached after 2 minutes after a blood pump stop. In the case of a pressure holding test, the blood pump rate can be lowered in good time before the test, the conveying rate of the blood pump and of the substitution pump can remain at a minimum during the bypass (e.g. pump stop) and both rates can be slowly ramped up to their desired value again after the bypass.

The invention claimed is:

1. A method of purging gas bubbles from at least one target zone of an extracorporeal blood circuit with a flushing liquid, characterized in that
    the flow rate of the flushing liquid in the extracorporeal blood circuit is periodically increased and reduced during the flushing process,
    the flow rate of the flushing liquid in the extracorporeal blood circuit lies outside a range of possible flow rates at least at times during the flushing process, which range is used during the treatment for the blood,
    the flow rate of the flushing liquid in the extracorporeal blood circuit at least at times during the flushing process is larger than 700 ml/min, and
    the flow rate of the flushing liquid in the extracorporeal blood circuit is increased and reduced in bursts.

2. A method in accordance with claim 1, characterized in that the flushing liquid is conveyed through the target zone using a pump; and in that the variation of the flow rate and/or of the pressure takes/take place by a change in the conveying rate of the pump.

3. A method in accordance with claim 2, characterized in that the change in the conveying rate takes place by a switching on and switching off of the pump or by a throttling and increasing of the pump speed.

4. A method in accordance with claim 2, characterized in that the pump is a blood pump arranged in the extracorporeal blood circuit or a flushing pump arranged outside the extracorporeal blood circuit.

5. A method in accordance with claim 1, characterized in that the extracorporeal blood circuit has at least one clamp or a valve; and in that the variation of the flow rate and/or of the pressure takes/take place by a control of the clamp or the valve.

6. A method in accordance with claim 1, characterized in that the bursts show a continuous or abrupt build-up and a continuous or abrupt drop in the flow rate and/or in the pressure of the flushing liquid.

7. A method in accordance with claim 1, characterized in that the amplitude of the bursts is selected such that the flow rate and/or the pressure of the flushing liquid varies between valleys and peaks by at least a factor of 1.3.

8. A method in accordance with claim 1, characterized in that the extracorporeal blood circuit is an extracorporeal blood circuit of a dialysis machine.

9. A method in accordance with claim 1, characterized in that the flow rate is periodically increased and reduced in periodic intervals of 2 seconds.

10. A method in accordance with claim 1, characterized in that the bursts have a duration of 0.1 to 5 seconds.

11. A method of purging gas bubbles from at least one target zone of an extracorporeal blood circuit with a flushing liquid, characterized in that
- the flow rate of the flushing liquid in the extracorporeal blood circuit is periodically increased and reduced during the flushing process,
- the flow rate of the flushing liquid in the extracorporeal blood circuit lies outside a range of possible flow rates at least at times during the flushing process, which range is used during the treatment for the blood,
- the flow rate of the flushing liquid in the extracorporeal blood circuit at least at times during the flushing process is larger than 700 ml/min,
- the flow rate of the flushing liquid in the extracorporeal blood circuit is increased and reduced in bursts,
- the flushing liquid is conveyed through the target zone using a pump, and
- the variation of the flow rate and/or of the pressure takes/take place by a throttling and increasing of the pump speed.

* * * * *